(12) United States Patent
Tunheim et al.

(10) Patent No.: US 9,222,892 B2
(45) Date of Patent: *Dec. 29, 2015

(54) SYSTEMS AND METHODS FOR MONITORING THE QUALITY OF A FLUID

(75) Inventors: Ola Tunheim, Bryne (NO); Robert P. Freese, Pittsboro, NC (US); James R. MacLennan, Aberdeen (GB)

(73) Assignee: Halliburton Energy Services, Inc., Houston, TX (US)

( * ) Notice: Subject to any disclaimer, the term of this patent is extended or adjusted under 35 U.S.C. 154(b) by 205 days.

This patent is subject to a terminal disclaimer.

(21) Appl. No.: 13/616,957

(22) Filed: Sep. 14, 2012

(65) Prior Publication Data

US 2013/0031964 A1 Feb. 7, 2013

Related U.S. Application Data

(63) Continuation-in-part of application No. 13/198,915, filed on Aug. 5, 2011, and a continuation-in-part of application No. 13/198,950, filed on Aug. 5, 2011, and a continuation-in-part of application No. 13/198,972, (Continued)

(51) Int. Cl.
*G01N 21/85* (2006.01)

(52) U.S. Cl.
CPC ...................................... *G01N 21/85* (2013.01)

(58) Field of Classification Search
CPC .......................... G01N 21/636; G01N 21/8507
See application file for complete search history.

(56) References Cited

U.S. PATENT DOCUMENTS

| | | | |
|---|---|---|---|
| 5,431,227 A | 7/1995 | Montgomery et al. | |
| 5,540,825 A | 7/1996 | Yeung et al. | |
| 5,680,900 A | 10/1997 | Nguyen et al. | |
| 5,737,076 A | 4/1998 | Glaus et al. | |
| 5,996,690 A | 12/1999 | Shaw et al. | |
| 6,016,191 A | 1/2000 | Ramos et al. | |
| 6,198,531 B1 | 3/2001 | Myrick et al. | |
| 6,268,911 B1 * | 7/2001 | Tubel ..................... E21B 23/03 250/256 |
| 6,529,276 B1 | 3/2003 | Myrick | |
| 6,729,400 B2 | 5/2004 | Mullins et al. | |
| 6,755,978 B2 | 6/2004 | Oddie | |
| 6,880,566 B2 | 4/2005 | Newman | |
| 7,123,844 B2 | 10/2006 | Myrick | |
| 7,138,156 B1 | 11/2006 | Myrick et al. | |
| 7,236,237 B2 | 6/2007 | Schmilovitch et al. | |

(Continued)

FOREIGN PATENT DOCUMENTS

| | | |
|---|---|---|
| EP | 1969326 | 9/2008 |
| EP | 2087328 | 8/2009 |

(Continued)

OTHER PUBLICATIONS

International Search Report and Written Opinion for PCT/US2012/047065 dated Jul. 16, 2013.

(Continued)

*Primary Examiner* — Angela M DiTrani
*Assistant Examiner* — Ashish Varma
(74) *Attorney, Agent, or Firm* — McDermott Will & Emery LLP; Scott Brown (57) ABSTRACT

Disclosed are systems and methods for monitoring a fluid having one or more adulterants therein. One method of monitoring the fluid includes containing the fluid within a flow path, the fluid including at least one adulterant present therein, optically interacting at least one integrated computational element with the fluid, thereby generating optically interacted light, receiving with at least one detector the optically interacted light, and generating with the at least one detector an output signal corresponding to a characteristic of the at least one adulterant in the fluid.

24 Claims, 2 Drawing Sheets

Related U.S. Application Data filed on Aug. 5, 2011, and a continuation-in-part of application No. 13/204,005, filed on Aug. 5, 2011, and a continuation-in-part of application No. 13/204,046, filed on Aug. 5, 2011, and a continuation-in-part of application No. 13/204,123, filed on Aug. 5, 2011, and a continuation-in-part of application No. 13/204,165, filed on Aug. 5, 2011, and a continuation-in-part of application No. 13/204,213, filed on Aug. 5, 2011, and a continuation-in-part of application No. 13/204,294, filed on Aug. 5, 2011.

(56) References Cited

U.S. PATENT DOCUMENTS

| | | |
|---|---|---|
| 7,332,094 B2 | 2/2008 | Abney et al. |
| 7,472,748 B2 | 1/2009 | Gdanski et al. |
| 7,623,233 B2 | 11/2009 | Freese et al. |
| 7,671,973 B2 | 3/2010 | Van Beek et al. |
| 7,697,141 B2 | 4/2010 | Jones et al. |
| 7,712,527 B2 | 5/2010 | Roddy |
| 7,789,171 B2 | 9/2010 | Grayson et al. |
| 7,834,312 B2 | 11/2010 | Lievois et al. |
| 7,834,999 B2 | 11/2010 | Myrick et al. |
| 7,911,605 B2 | 3/2011 | Myrick et al. |
| 7,920,258 B2 | 4/2011 | Myrick et al. |
| 7,934,556 B2 | 5/2011 | Clark et al. |
| 8,049,881 B2 | 11/2011 | Myrick et al. |
| 8,141,633 B2 | 3/2012 | Hampton et al. |
| 8,253,619 B2 | 8/2012 | Holbrook et al. |
| 8,345,234 B2 | 1/2013 | Myrick et al. |
| 8,547,556 B2 | 10/2013 | Irani |
| 8,780,352 B2 | 7/2014 | Freese et al. |
| 8,823,939 B2 | 9/2014 | Freese et al. |
| 8,879,053 B2 | 11/2014 | Freese et al. |
| 8,908,165 B2 | 12/2014 | Tunheim et al. |
| 8,912,477 B2 | 12/2014 | Freese et al. |
| 8,941,046 B2 | 1/2015 | Freese et al. |
| 8,960,294 B2 | 2/2015 | Freese et al. |
| 8,997,860 B2 | 4/2015 | Freese et al. |
| 9,013,698 B2 | 4/2015 | Freese et al. |
| 9,013,702 B2 | 4/2015 | Freese et al. |
| 9,019,501 B2 | 4/2015 | Freese et al. |
| 9,074,990 B2 | 7/2015 | Freese et al. |
| 9,080,943 B2 | 7/2015 | Freese et al. |
| 2001/0020675 A1 | 9/2001 | Tubel et al. |
| 2001/0023614 A1 | 9/2001 | Tubel et al. |
| 2002/0023752 A1 | 2/2002 | Qu et al. |
| 2002/0109080 A1 | 8/2002 | Tubel et al. |
| 2003/0056581 A1 | 3/2003 | Turner et al. |
| 2003/0143580 A1 | 7/2003 | Straus |
| 2003/0145988 A1 | 8/2003 | Mullins et al. |
| 2004/0045705 A1 | 3/2004 | Gardner et al. |
| 2004/0129884 A1 | 7/2004 | Boyle et al. |
| 2004/0179194 A1 | 9/2004 | Schmilovitch et al. |
| 2006/0102343 A1 | 5/2006 | Skinner et al. |
| 2006/0142955 A1 | 6/2006 | Jones et al. |
| 2006/0158734 A1 | 7/2006 | Schuurmans et al. |
| 2007/0095528 A1 | 5/2007 | Ziauddin et al. |
| 2007/0114372 A1 | 5/2007 | Lievois et al. |
| 2007/0177240 A1 | 8/2007 | Van Beek et al. |
| 2007/0215385 A1 | 9/2007 | Anderson |
| 2007/0281870 A1 | 12/2007 | Robb et al. |
| 2007/0282647 A1 | 12/2007 | Freese et al. |
| 2007/0291251 A1 | 12/2007 | Rensen et al. |
| 2008/0000635 A1 | 1/2008 | Rioufol et al. |
| 2008/0041594 A1 | 2/2008 | Boles et al. |
| 2008/0094623 A1 | 4/2008 | Schuurmans et al. |
| 2008/0133193 A1 | 6/2008 | Gdanski et al. |
| 2008/0166720 A1 | 7/2008 | Hsieh et al. |
| 2008/0217011 A1 | 9/2008 | Pauls et al. |
| 2008/0231849 A1 | 9/2008 | Myrick et al. |
| 2008/0262737 A1 | 10/2008 | Thigpen et al. |
| 2008/0276687 A1 | 11/2008 | Myrick et al. |
| 2008/0309930 A1 | 12/2008 | Rensen |
| 2009/0002697 A1 | 1/2009 | Freese et al. |
| 2009/0015819 A1 | 1/2009 | Van Beek et al. |
| 2009/0033933 A1 | 2/2009 | Myrick et al. |
| 2009/0073433 A1 | 3/2009 | Myrick et al. |
| 2009/0087912 A1 | 4/2009 | Ramos et al. |
| 2009/0097024 A1 | 4/2009 | Blackburn et al. |
| 2009/0140144 A1 | 6/2009 | Myrick et al. |
| 2009/0154288 A1 | 6/2009 | Heathman |
| 2009/0182693 A1 | 7/2009 | Fulton et al. |
| 2009/0205821 A1 | 8/2009 | Smith |
| 2009/0216504 A1 | 8/2009 | Priore et al. |
| 2009/0219512 A1 | 9/2009 | Myrick et al. |
| 2009/0219538 A1 | 9/2009 | Myrick et al. |
| 2009/0219539 A1 | 9/2009 | Myrick et al. |
| 2009/0219597 A1 | 9/2009 | Myrick et al. |
| 2009/0245718 A1* | 10/2009 | Li .................. B82Y 20/00 385/12 |
| 2009/0250613 A1 | 10/2009 | Myrick et al. |
| 2009/0299946 A1 | 12/2009 | Myrick et al. |
| 2009/0305330 A1 | 12/2009 | Kroon et al. |
| 2009/0316150 A1 | 12/2009 | Myrick et al. |
| 2010/0006292 A1 | 1/2010 | Boles et al. |
| 2010/0042348 A1 | 2/2010 | Bakker |
| 2010/0050905 A1 | 3/2010 | Lewis et al. |
| 2010/0051266 A1 | 3/2010 | Roddy et al. |
| 2010/0051275 A1 | 3/2010 | Lewis et al. |
| 2010/0073666 A1 | 3/2010 | Perkins et al. |
| 2010/0084132 A1 | 4/2010 | Noya et al. |
| 2010/0141952 A1 | 6/2010 | Myrick et al. |
| 2010/0148785 A1* | 6/2010 | Schaefer ............ G01V 8/02 324/338 |
| 2010/0149523 A1 | 6/2010 | Heideman et al. |
| 2010/0149537 A1 | 6/2010 | Myrick et al. |
| 2010/0153048 A1 | 6/2010 | Myrick et al. |
| 2010/0182600 A1 | 7/2010 | Freese et al. |
| 2010/0195105 A1 | 8/2010 | Myrick et al. |
| 2010/0245096 A1 | 9/2010 | Jones et al. |
| 2010/0265509 A1 | 10/2010 | Jones et al. |
| 2010/0269579 A1 | 10/2010 | Lawrence et al. |
| 2010/0285105 A1 | 11/2010 | Radianingtyas |
| 2010/0302539 A1 | 12/2010 | Myrick et al. |
| 2010/0305741 A1 | 12/2010 | Myrick |
| 2010/0326659 A1 | 12/2010 | Schultz et al. |
| 2010/0328669 A1 | 12/2010 | Myrick et al. |
| 2011/0042320 A1 | 2/2011 | Allen |
| 2011/0048708 A1 | 3/2011 | Glasbergen et al. |
| 2011/0163046 A1 | 7/2011 | Neal et al. |
| 2011/0166046 A1 | 7/2011 | Weaver et al. |
| 2011/0197662 A1* | 8/2011 | McAlister ................ 73/61.59 |
| 2011/0199610 A1 | 8/2011 | Myrick et al. |
| 2011/0212512 A1 | 9/2011 | Wang et al. |
| 2011/0312012 A1 | 12/2011 | Skinderso et al. |
| 2012/0000643 A1 | 1/2012 | Bruun et al. |
| 2012/0135396 A1 | 5/2012 | McDevitt et al. |
| 2012/0150451 A1 | 6/2012 | Skinner et al. |
| 2012/0160329 A1 | 6/2012 | MacKenzie et al. |
| 2012/0250017 A1 | 10/2012 | Morys et al. |
| 2013/0031964 A1 | 2/2013 | Tunheim et al. |
| 2013/0031970 A1 | 2/2013 | Freese et al. |
| 2013/0031971 A1 | 2/2013 | Freese et al. |
| 2013/0031972 A1 | 2/2013 | Freese et al. |
| 2013/0032333 A1 | 2/2013 | Freese et al. |
| 2013/0032340 A1 | 2/2013 | Freese et al. |
| 2013/0032344 A1 | 2/2013 | Freese et al. |
| 2013/0032345 A1 | 2/2013 | Freese et al. |
| 2013/0033701 A1 | 2/2013 | Tunheim et al. |
| 2013/0033702 A1 | 2/2013 | Tunheim et al. |
| 2013/0034842 A1 | 2/2013 | Tunheim et al. |
| 2013/0284895 A1 | 10/2013 | Freese et al. |
| 2014/0263974 A1 | 9/2014 | Freese et al. |

FOREIGN PATENT DOCUMENTS

| | | |
|---|---|---|
| EP | 2140238 | 1/2010 |
| EP | 2320027 A1 | 5/2011 |
| FR | 2954563 A1 | 6/2011 |
| GB | 2353310 A | 2/2001 |
| JP | 2009284813 A | 12/2009 |
| WO | 9850680 A2 | 11/1998 |

(56) References Cited

FOREIGN PATENT DOCUMENTS

| WO | 2004018840 A1 | 3/2004 |
|---|---|---|
| WO | 2006137902 A2 | 12/2006 |
| WO | 2006137902 A3 | 12/2006 |
| WO | 2007064575 | 6/2007 |
| WO | 2008121715 A1 | 10/2008 |
| WO | 2009055200 A2 | 4/2009 |
| WO | 2009055220 A2 | 4/2009 |
| WO | 2009077758 A1 | 6/2009 |
| WO | 2011063086 A1 | 5/2011 |
| WO | 2014042909 A1 | 3/2014 |
| WO | 2014042933 A1 | 3/2014 |
| WO | 2014043010 A1 | 3/2014 |
| WO | 2014043050 A1 | 3/2014 |
| WO | 2014043057 A1 | 3/2014 |

OTHER PUBLICATIONS

International Search Report and Written Opinion for PCT/US2012/045677 dated Jul. 16, 2013.
Official Action for Australian Patent Application 2012294881 dated May 22, 2014.
International Search Report and Written Opinion for PCT/US2013/057832 dated Nov. 22, 2013.
International Search Report and Written Opinion for PCT/US2013/058041 dated Dec. 2, 2013.
International Search Report and Written Opinion for PCT/US2013/058700 dated Dec. 6, 2013.
International Search Report and Written Opinion for PCT/US2013/058864 dated Dec. 16, 2013.
International Preliminary Report on Patentability for PCT/US2012/046892 dated Feb. 20, 2014.
International Search Report and Written Opinion for PCT/US2012/044148 dated Oct. 4, 2012.
Myrick, et al. "Spectral Tolerance Determination for Multivariate Optical Element Design," Fresenuis' Journal of Analytical Chemistry, 369:2001; pp. 351-355.
Gdanski et al., "A New Model for Matching Fracturing Fluid Flowback Composition," 2007 SPE Hydraulic Fracturing Technology Conference held in College Station, Texas, SPE 106040.
Gdanski et al., "Using Lines-of-Solutions to Understand Fracture Conductivity and Fracture Cleanup," SPE Production and Operations Symposium held in Oklahoma City, OK, 2011, SPE 142096.
Ramachandran et al., "Chemical Kinetics in Real Time: Using the Differential Rate Law and Discovering the Reaction Orders," A Physical chemistry Laboratory Experiment, Journal of chemical Education; 1996, pp. 686-689.
Official Action for Australian Patent Application No. 2013 252841 dated Nov. 10, 2014.
Official Action for Australian Patent Application No. 2013 252881 dated Nov. 12, 2014.
Official Action for Australian Patent Application No. 2013252855 dated Apr. 15, 2015.
Dai et al., Molecular Factor Computing for Predictive Spectroscopy, Pharmaceutical Research, vol. 24, No. 8, 2007, pp. 1441-1449.
Mendendorp J., et al., Application of Integrated Sensing and Processing in Spectroscopic Imaging and Sensing, Journal of Chemometrics, vol. 19, 2005, pp. 533-542.
Official Action for Singapore Patent Application No. 11201500780V dated Jun. 16, 2015.
Official Action for New Zealand Patent Application No. NZ 704529 dated Jun. 9, 2015.
Official Action for Canadian Patent Application No. CA 2,842,191 dated May 6, 2015.

\* cited by examiner

SYSTEMS AND METHODS FOR MONITORING THE QUALITY OF A FLUID

CROSS-REFERENCE TO RELATED APPLICATIONS

The present application claims priority to and is a continuation-in-part application of co-owned U.S. patent application Ser. Nos. 13/198,915; 13/198,950; 13/198,972; 13/204,005; 13/204,046; 13/204,123; 13/204,165; 13/204,213; and 13/204,294, each of which were filed on Aug. 5, 2011. The contents of each priority application are hereby incorporated by reference.

BACKGROUND

The present invention relates to methods for monitoring a fluid in or near real-time and, more specifically, to methods for monitoring a fluid having one or more adulterants therein.

In the oil and gas industry, it can be important to precisely know the characteristics and chemical composition of fluids circulating into and out of subterranean hydrocarbon-bearing formations. Typically, the analysis of fluids related to the oil and gas industry has been conducted off-line using laboratory analyses, such as spectroscopic and/or wet chemical methods, which analyze an extracted sample of the fluid. Depending on the analysis required, however, such an approach can take hours to days to complete, and even in the best case scenario, a job will often be completed prior to the analysis being obtained. Furthermore, off-line laboratory analyses can sometimes be difficult to perform, require extensive sample preparation and present hazards to personnel performing the analyses.

Although off-line, retrospective analyses can be satisfactory in certain cases, but they nonetheless do not allow real-time or near real-time analysis capabilities. As a result, proactive control of a subterranean operation or fluid flow cannot take place, at least without significant process disruption occurring while awaiting the results of the analysis. Off-line, retrospective analyses can also be unsatisfactory for determining true characteristics of a fluid since the characteristics of the extracted sample of the fluid oftentimes changes during the lag time between collection and analysis, thereby making the properties of the sample non-indicative of the true chemical composition or characteristic. For example, factors that can alter the characteristics of a fluid during the lag time between collection and analysis can include, for example, scaling, reaction of various components in the fluid with one another, reaction of various components in the fluid with components of the surrounding environment, simple chemical degradation, and bacterial growth.

Monitoring fluids in or near real-time can be of considerable interest in order to monitor how the fluids change over time, thereby serving as a quality control measure for processes in which fluids are used. Specifically, adulterants present in the fluid can lead to harmful scale formation, impurity buildup, and bacterial growth which can impede processes in which the fluid is used, and even damage process equipment in certain cases. For example, water streams used in cooling towers and similar processes can become highly corrosive over time and become susceptible to scale formation and bacterial growth. Corrosion and scale formation can damage pipelines through which the water is flowing and potentially lead to system breakdowns. Similar issues can be encountered for fluids subjected to other types of environments.

Spectroscopic techniques for measuring various characteristics of fluids are well known and are routinely used under laboratory conditions. In some cases, these spectroscopic techniques can be carried out without using an involved sample preparation. It is more common, however, to carry out various sample preparation procedures before conducting the analysis. Thus, there is usually a delay in obtaining an analysis due to sample preparation time, even discounting the transit time of transporting the extracted sample to a laboratory. Although spectroscopic techniques can, at least in principle, be conducted at a job site, such as a well site, or in a process, the foregoing concerns regarding sample preparation times may still apply. Furthermore, the transitioning of spectroscopic instruments from a laboratory into a field or process environment can be expensive and complex. Reasons for these issues can include, for example, the need to overcome inconsistent temperature, humidity, and vibration encountered during field use. Furthermore, sample preparation, when required, can be difficult under field analysis conditions. The difficulty of performing sample preparation in the field can be especially problematic in the presence of interfering materials, which can further complicate conventional spectroscopic analyses.

SUMMARY OF THE INVENTION

The present invention relates to methods for monitoring a fluid in or near real-time and, more specifically, to methods for monitoring a fluid having one or more adulterants therein.

In some aspects of the disclosure, a system is disclosed that includes a flow path containing a fluid having at least one adulterant present therein, at least one integrated computational element configured to optically interact with the fluid and thereby generate optically interacted light, and at least one detector arranged to receive the optically interacted light and generate an output signal corresponding to a characteristic of the at least one adulterant within the fluid.

In other aspects, a method of monitoring a fluid is disclosed. The method may include containing the fluid within a flow path, the fluid including at least one adulterant present therein, optically interacting electromagnetic radiation from the fluid with at least one integrated computational element, thereby generating optically interacted light, receiving with at least one detector the optically interacted light, and generating with the at least one detector an output signal corresponding to a characteristic of the at least one adulterant in the fluid.

In yet other aspects of the disclosure, a method of monitoring a quality of a fluid is disclosed. The method may include optically interacting an electromagnetic radiation source with a fluid contained within a flow path and at least one integrated computational element, thereby generating optically interacted light, receiving with at least one detector the optically interacted light, measuring a characteristic of at least one known adulterant in the fluid with the at least one detector, generating an output signal corresponding to the characteristic of the at least one known adulterant, and undertaking at least one corrective step when the characteristic of the at least one adulterant surpasses a predetermined range of suitable operation.

The features and advantages of the present invention will be readily apparent to those skilled in the art upon a reading of the description of the preferred embodiments that follows.

BRIEF DESCRIPTION OF THE DRAWINGS

The following figures are included to illustrate certain aspects of the present invention, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

The present invention relates to methods for monitoring a fluid in or near real-time and, more specifically, to methods for monitoring a fluid having one or more adulterants therein.

The exemplary systems and methods described herein employ various configurations of optical computing devices, also commonly referred to as "opticoanalytical devices," for the real-time or near real-time monitoring of a fluid. In operation, the exemplary systems and methods may be useful and otherwise advantageous in determining product quality of the fluid. For example, the optical computing devices, which are described in more detail below, can advantageously provide real-time or near real-time fluid monitoring that cannot presently be achieved with either onsite analyses at a job site or via more detailed analyses that take place in a laboratory. A significant and distinct advantage of these devices is that they can be configured to specifically detect and/or measure a particular component or characteristic of interest of a fluid, such as a known adulterant, thereby allowing qualitative and/or quantitative analyses of the fluid to occur without having to extract a sample and undertake time-consuming analyses of the sample at an off-site laboratory. With the ability to undertake real-time or near real-time analyses, the exemplary systems and methods described herein may be able to provide some measure of proactive or responsive control over the fluid flow, enable the collection and archival of fluid information in conjunction with operational information to optimize subsequent operations, and/or enhance the capacity for remote job execution.

Those skilled in the art will readily appreciate that the systems and methods disclosed herein may be suitable for use in the oil and gas industry since the described optical computing devices provide a cost-effective, rugged, and accurate means for monitoring hydrocarbon quality in order to facilitate the efficient management of oil/gas production. It will be further appreciated, however, that the various disclosed systems and methods are equally applicable to other technology or industry fields including, but not limited to, the food, medical, and drug industries, industrial applications, pollution mitigation, recycling industries, mining industries, security and military industries, or any field where it may be advantageous to determine in real-time or near real-time the concentration or a characteristic of a specific substance in a flowing fluid. In at least one embodiment, for example, the present systems and methods may be employed to monitor the quality of potable water. In other embodiments, the present systems and methods may be employed to monitor soil quality, such as in the agricultural industry where the quality of soil is often measured for concentrations of potassium, phosphates, and other minerals in order to determine fertilizations needs. Soil quality may also be monitored to determine pollution levels present therein, such as in the event of an oil spill or the like.

The optical computing devices suitable for use in the present embodiments can be deployed at any number of various points within a flow path to monitor the fluid and the various changes that may occur thereto between two or more points. Depending on the location of the particular optical computing device, various types of information about the fluid can be obtained. In some cases, for example, the optical computing devices can be used to monitor changes to the fluid as a result of adding a treatment substance thereto, removing a treatment substance therefrom, or exposing the fluid to a condition that potentially changes a characteristic of the fluid in some way. In other cases, product quality of the fluid may be obtained by identifying and quantifying the concentration of known adulterants that may be present in the fluid. Thus, the systems and methods described herein may be configured to monitor a flow of fluids and, more particularly, to monitor the present state of the fluid and any changes thereto with respect to the influx or presence of known adulterants therein.

As used herein, the term "fluid" refers to any substance that is capable of flowing, including particulate solids, liquids, gases, slurries, emulsions, powders, muds, glasses, combinations thereof, and the like. In some embodiments, the fluid can be an aqueous fluid, including water or the like. In some embodiments, the fluid can be a non-aqueous fluid, including organic compounds, more specifically, hydrocarbons, oil, a refined component of oil, petrochemical products, and the like. In some embodiments, the fluid can be a treatment fluid or a formation fluid as found in the oil and gas industry. Fluids can include various flowable mixtures of solids, liquids and/or gases. Illustrative gases that can be considered fluids according to the present embodiments include, for example, air, nitrogen, carbon dioxide, argon, helium, methane, ethane, butane, and other hydrocarbon gases, combinations thereof and/or the like.

As used herein, the term "characteristic" refers to a chemical, mechanical, or physical property of a substance. A characteristic of a substance may include a quantitative value of one or more chemical components therein. Such chemical components may be referred to herein as "analytes." Illustrative characteristics of a substance that can be monitored with the optical computing devices disclosed herein can include, for example, chemical composition (e.g., identity and concentration in total or of individual components), impurity content, pH, viscosity, density, ionic strength, total dissolved solids, salt content, porosity, opacity, bacteria content, combinations thereof, and the like. Moreover, the phrase "characteristic of interest of/in a fluid" may be used herein to refer to the characteristic of a substance contained in or otherwise flowing with the fluid.

As used herein, the term "flow path" refers to a route through which a fluid is capable of being transported between two points. In some cases, the flow path need not be continuous or otherwise contiguous between the two points. Exemplary flow paths include, but are not limited to, a flowline, a pipeline, a hose, a process facility, a storage vessel, a tanker, a railway tank car, a transport ship or vessel, a trough, a stream, a sewer, a subterranean formation, etc., combinations thereof, or the like. In cases where the flow path is a pipeline, or the like, the pipeline may be a pre-commissioned pipeline or an operational pipeline. In other cases, the flow path may be created or generated via movement of an optical computing device through a fluid (e.g., an open air sensor). In yet other cases, the flow path is not necessarily contained within any rigid structure, but may refer to the path fluid takes between two points, such as where a fluid flows from one location to another without being contained, per se. It should be noted that the term "flow path" does not necessarily imply that a fluid is flowing therein, rather that a fluid is capable of being transported or otherwise flowable therethrough.

As used herein, the term "adulterant," or variations thereof, refers to at least a portion of a substance or chemical within the fluid to be evaluated using the optical computing devices described herein. In some embodiments, the adulterant is the characteristic of interest, as defined above, and may therefore be used interchangeably therewith herein. In some aspects, the adulterant includes any integral or non-integral component of the fluid flowing within the flow path which may or may not be considered damaging or otherwise disadvantageous to the fluid. In one or more embodiments, the adulterant may include substances or chemicals such as BTEX compounds (i.e., benzene, toluene, ethylbenzene, and xylenes), volatile organic compounds (VOCs), naphthalene, styrene, sulfur compounds, hexane, liquefiable hydrocarbons, barium, calcium, manganese, sulfur, iron, strontium, chlorine, potassium, phosphor, magnesium, boron, copper, molybdenum, zinc, carbon, hydrogen, oxygen, combinations thereof, or the like. In other embodiments, the adulterant may include or otherwise refer to paraffins, waxes, asphaltenes, aromatics, saturates, foams, salts, bacteria, particulates, sand or other solid particles, pipe coatings (e.g., polymers), combinations thereof, and the like. In other embodiments, the adulterant may refer to various flow path "tags" added, such as nanoparticles or the like.

In other aspects, the adulterant may include any substance or chemical added to the flow path in order to treat the flow path for flow assurance reasons. Exemplary treatment substances may include, but are not limited to, acids, acid-generating compounds, bases, base-generating compounds, biocides, surfactants, scale inhibitors, corrosion inhibitors, gelling agents, exothermic substances, crosslinking agents, anti-sludging agents, foaming agents, defoaming agents, antifoam agents, emulsifying agents, de-emulsifying agents, iron control agents, proppants or other particulates, gravel, particulate diverters, salts, fluid loss control additives, gases, catalysts, clay control agents, chelating agents, corrosion inhibitors, dispersants, flocculants, scavengers (e.g., $H_2S$ scavengers, $CO_2$ scavengers or $O_2$ scavengers), lubricants, breakers, delayed release breakers, friction reducers, bridging agents, viscosifiers, weighting agents, solubilizers, rheology control agents, viscosity modifiers, pH control agents (e.g., buffers), hydrate inhibitors, relative permeability modifiers, diverting agents, consolidating agents, fibrous materials, bactericides, tracers, probes, nanoparticles, and the like. Combinations of these substances can be used as well.

As used herein, the term "electromagnetic radiation" refers to radio waves, microwave radiation, infrared and near-infrared radiation, visible light, ultraviolet light, X-ray radiation and gamma ray radiation.

As used herein, the term "optical computing device" refers to an optical device that is configured to receive an input of electromagnetic radiation from a fluid, or a substance or adulterant within the fluid, and produce an output of electromagnetic radiation from a processing element arranged within the optical computing device. The processing element may be, for example, an integrated computational element (ICE) used in the optical computing device. As discussed in greater detail below, the electromagnetic radiation that optically interacts with the processing element is changed so as to be readable by a detector, such that an output of the detector can be correlated to at least one adulterant measured or monitored within the fluid. The output of electromagnetic radiation from the processing element can be reflected electromagnetic radiation, transmitted electromagnetic radiation, and/or dispersed electromagnetic radiation. Whether reflected, transmitted, or dispersed electromagnetic radiation is eventually analyzed by the detector may be dictated by the structural parameters of the optical computing device as well as other considerations known to those skilled in the art. In addition, emission and/or scattering of the substance, for example via fluorescence, luminescence, Raman scattering, and/or Raleigh scattering, can also be monitored by the optical computing devices.

As used herein, the term "optically interact" or variations thereof refers to the reflection, transmission, scattering, diffraction, or absorption of electromagnetic radiation either on, through, or from one or more processing elements (i.e., integrated computational elements). Accordingly, optically interacted light refers to light that has been reflected, transmitted, scattered, diffracted, or absorbed by, emitted, or re-radiated, for example, using the integrated computational elements, but may also apply to interaction with a fluid or an adulterant within the fluid.

The exemplary systems and methods described herein will include at least one optical computing device arranged along or in a flow path in order to monitor a fluid flowing or otherwise contained therein. Each optical computing device may include an electromagnetic radiation source, at least one processing element (e.g., integrated computational elements), and at least one detector arranged to receive optically interacted light from the at least one processing element. As disclosed below, however, in at least one embodiment, the electromagnetic radiation source may be omitted and instead the electromagnetic radiation may be derived from the fluid or adulterant itself. In some embodiments, the exemplary optical computing devices may be specifically configured for detecting, analyzing, and quantitatively measuring a particular characteristic, adulterant, or analyte of interest of the fluid in the flow path. In other embodiments, the optical computing devices may be general purpose optical devices, with post-acquisition processing (e.g., through computer means) being used to specifically detect the characteristic of the sample.

In some embodiments, suitable structural components for the exemplary optical computing devices are described in commonly owned U.S. Pat. Nos. 6,198,531; 6,529,276; 7,123,844; 7,834,999; 7,911,605; 7,920,258; and 8,049,881, each of which is incorporated herein by reference in its entirety, and U.S. patent application Ser. Nos. 12/094,460; 12/094,465; and 13/456,467, each of which is also incorporated herein by reference in its entirety. As will be appreciated, variations of the structural components of the optical computing devices described in the above-referenced patents and patent applications may be suitable, without departing from the scope of the disclosure, and therefore, should not be considered limiting to the various embodiments or uses disclosed herein.

The optical computing devices described in the foregoing patents and patent applications combine the advantage of the power, precision and accuracy associated with laboratory spectrometers, while being extremely rugged and suitable for field use. Furthermore, the optical computing devices can perform calculations (analyses) in real-time or near real-time without the need for time-consuming sample processing. In this regard, the optical computing devices can be specifically configured to detect and analyze particular characteristics, adulterants, and/or analytes of interest of a fluid. As a result, interfering signals are discriminated from those of interest in the substance by appropriate configuration of the optical computing devices, such that the optical computing devices provide a rapid response regarding the characteristics of the fluid as based on the detected output. In some embodiments, the detected output can be converted into a voltage that is distinctive of the magnitude of the characteristic or adulterant being monitored in the fluid. The foregoing advantages and others make the optical computing devices particularly well suited for field and downhole use, but may equally be applied to several other technologies or industries, without departing from the scope of the disclosure.

The optical computing devices can be configured to detect not only the composition and concentrations of an adulterant in a fluid, but they also can be configured to determine physical properties and other characteristics of the adulterant as well, based on their analysis of the electromagnetic radiation received from the particular adulterant. For example, the optical computing devices can be configured to determine the concentration of an analyte and correlate the determined concentration to a characteristic of an adulterant by using suitable processing means. As will be appreciated, the optical computing devices may be configured to detect as many adulterants or as many characteristics or analytes of the adulterant as desired in the fluid. All that is required to accomplish the monitoring of multiple characteristics and/or adulterants is the incorporation of suitable processing and detection means within the optical computing device for each adulterant and/or characteristic. In some embodiments, the properties of the adulterant can be a combination of the properties of the analytes therein (e.g., a linear, non-linear, logarithmic, and/or exponential combination). Accordingly, the more characteristics and analytes that are detected and analyzed using the optical computing devices, the more accurately the properties of the given adulterant will be determined.

The optical computing devices described herein utilize electromagnetic radiation to perform calculations, as opposed to the hardwired circuits of conventional electronic processors. When electromagnetic radiation interacts with an adulterant in a fluid, unique physical and chemical information about the adulterant may be encoded in the electromagnetic radiation that is reflected from, transmitted through, or radiated from the adulterant. This information is often referred to as the spectral "fingerprint" of the adulterant. The optical computing devices described herein are capable of extracting the information of the spectral fingerprint of multiple characteristics or analytes within an adulterant, and converting that information into a detectable output relating to one or more properties of the adulterant. That is, through suitable configurations of the optical computing devices, electromagnetic radiation associated with a characteristic or analyte of interest of an adulterant can be separated from electromagnetic radiation associated with all other components of the fluid in order to estimate the properties of the adulterant in real-time or near real-time.

Figure 1:
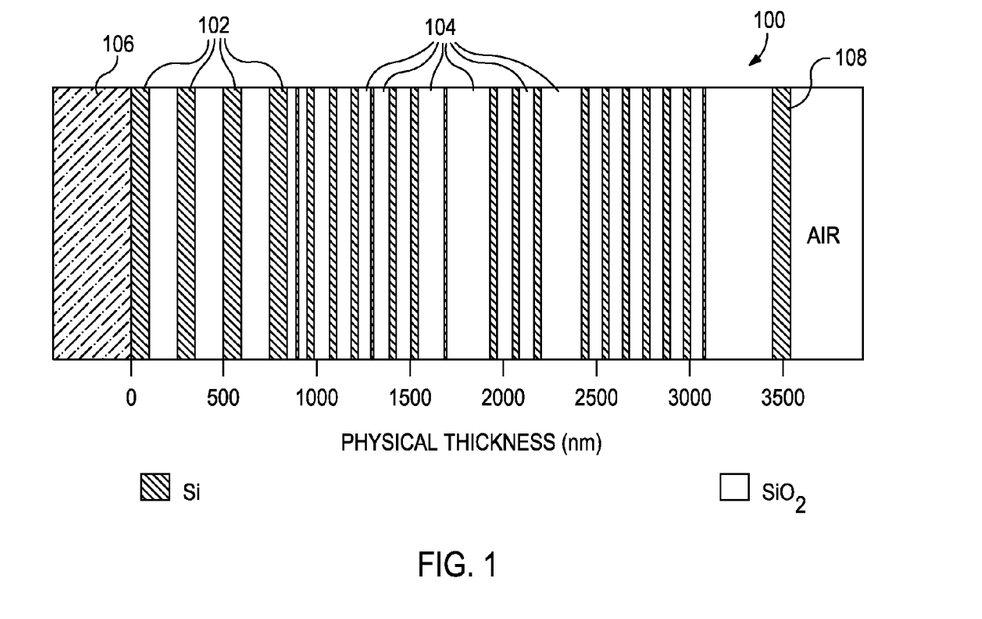
FIG. 1 illustrates an exemplary integrated computation element, according to one or more embodiments.

The processing elements used in the exemplary optical computing devices described herein may be characterized as integrated computational elements (ICE). Each ICE is capable of distinguishing electromagnetic radiation related to the characteristic or adulterant of interest from electromagnetic radiation related to other components of a fluid. Referring to FIG. 1, illustrated is an exemplary ICE 100 suitable for use in the optical computing devices used in the systems and methods described herein. As illustrated, the ICE 100 may include a plurality of alternating layers 102 and 104, such as silicon (Si) and $SiO_2$ (quartz), respectively. In general, these layers 102, 104 consist of materials whose index of refraction is high and low, respectively. Other examples might include niobia and niobium, germanium and germania, MgF, SiO, and other high and low index materials known in the art. The layers 102, 104 may be strategically deposited on an optical substrate 106. In some embodiments, the optical substrate 106 is BK-7 optical glass. In other embodiments, the optical substrate 106 may be another type of optical substrate, such as quartz, sapphire, silicon, germanium, zinc selenide, zinc sulfide, or various plastics such as polycarbonate, polymethylmethacrylate (PMMA), polyvinylchloride (PVC), diamond, ceramics, combinations thereof, and the like.

At the opposite end (e.g., opposite the optical substrate 106 in FIG. 1), the ICE 100 may include a layer 108 that is generally exposed to the environment of the device or installation. The number of layers 102, 104 and the thickness of each layer 102, 104 are determined from the spectral attributes acquired from a spectroscopic analysis of a characteristic of the adulterant using a conventional spectroscopic instrument. The spectrum of interest of a given characteristic of an adulterant typically includes any number of different wavelengths. It should be understood that the exemplary ICE 100 in FIG. 1 does not in fact represent any particular characteristic of a given adulterant, but is provided for purposes of illustration only. Consequently, the number of layers 102, 104 and their relative thicknesses, as shown in FIG. 1, bear no correlation to any particular characteristic of a given adulterant. Nor are the layers 102, 104 and their relative thicknesses necessarily drawn to scale, and therefore should not be considered limiting of the present disclosure. Moreover, those skilled in the art will readily recognize that the materials that make up each layer 102, 104 (i.e., Si and $SiO_2$) may vary, depending on the application, cost of materials, and/or applicability of the material to the given adulterant.

In some embodiments, the material of each layer 102, 104 can be doped or two or more materials can be combined in a manner to achieve the desired optical characteristic. In addition to solids, the exemplary ICE 100 may also contain liquids and/or gases, optionally in combination with solids, in order to produce a desired optical characteristic. In the case of gases and liquids, the ICE 100 can contain a corresponding vessel (not shown), which houses the gases or liquids. Exemplary variations of the ICE 100 may also include holographic optical elements, gratings, piezoelectric, light pipe, digital light pipe (DLP), and/or acousto-optic elements, for example, that can create transmission, reflection, and/or absorptive properties of interest.

The multiple layers 102, 104 exhibit different refractive indices. By properly selecting the materials of the layers 102, 104 and their relative thickness and spacing, the ICE 100 may be configured to selectively pass/reflect/refract predetermined fractions of electromagnetic radiation at different wavelengths. Each wavelength is given a predetermined weighting or loading factor. The thickness and spacing of the layers 102, 104 may be determined using a variety of approximation methods from the spectrograph of the characteristic or analyte of interest. These methods may include inverse Fourier transform (IFT) of the optical transmission spectrum and structuring the ICE 100 as the physical representation of the IFT. The approximations convert the IFT into a structure based on known materials with constant refractive indices. Further information regarding the structures and design of exemplary integrated computational elements (also referred to as multivariate optical elements) is provided in *Applied Optics*, Vol. 35, pp. 5484-5492 (1996) and Vol. 129, pp. 2876-2893, which is hereby incorporated by reference.

The weightings that the layers 102, 104 of the ICE 100 apply at each wavelength are set to the regression weightings described with respect to a known equation, or data, or spectral signature. Briefly, the ICE 100 may be configured to perform the dot product of the input light beam into the ICE 100 and a desired loaded regression vector represented by each layer 102, 104 for each wavelength. As a result, the output light intensity of the ICE 100 is related to the characteristic or analyte of interest. Further details regarding how the exemplary ICE 100 is able to distinguish and process electromagnetic radiation related to the characteristic or analyte of interest are described in U.S. Pat. Nos. 6,198,531; 6,529,276; and 7,920,258, previously incorporated herein by reference.

Figure 2:
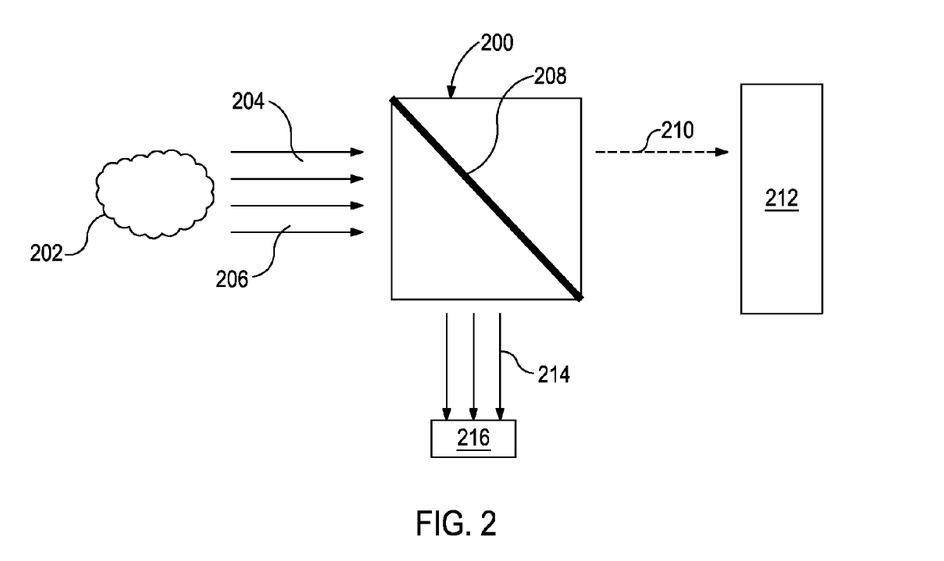
FIG. 2 illustrates a block diagram non-mechanistically illustrating how an optical computing device distinguishes electromagnetic radiation related to a characteristic of interest from other electromagnetic radiation, according to one or more embodiments.

Referring now to FIG. 2, illustrated is a block diagram that non-mechanistically illustrates how an optical computing device 200 is able to distinguish electromagnetic radiation related to a characteristic or adulterant of a fluid from other electromagnetic radiation. As shown in FIG. 2, after being illuminated with incident electromagnetic radiation, a fluid 202 containing an adulterant (e.g., a characteristic of interest) produces an output of electromagnetic radiation (e.g., sample-interacted light), some of which is electromagnetic radiation 204 relating to the adulterant and some of which is background electromagnetic radiation 206 corresponding to other components or characteristics of the fluid 202.

Although not specifically shown, one or more spectral elements may be employed in the device 200 in order to restrict the optical wavelengths and/or bandwidths of the system and thereby eliminate unwanted electromagnetic radiation existing in wavelength regions that have no importance. Such spectral elements can be located anywhere along the optical train, but are typically employed directly after the light source, which provides the initial electromagnetic radiation. Various configurations and applications of spectral elements in optical computing devices may be found in commonly owned U.S. Pat. Nos. 6,198,531; 6,529,276; 7,123,844; 7,834,999; 7,911,605, 7,920,258, 8,049,881, and U.S. patent application Ser. Nos. 12/094,460 (U.S. Pat. App. Pub. No. 2009/0219538); Ser. No. 12/094,465 (U.S. Pat. App. Pub. No. 2009/0219539); and Ser. No. 13/456,467, incorporated herein by reference, as indicated above.

The beams of electromagnetic radiation 204, 206 impinge upon the optical computing device 200, which contains an exemplary ICE 208 therein. In the illustrated embodiment, the ICE 208 may be configured to produce optically interacted light, for example, transmitted optically interacted light 210 and reflected optically interacted light 214. In operation, the ICE 208 may be configured to distinguish the electromagnetic radiation 204 from the background electromagnetic radiation 206.

The transmitted optically interacted light 210, which may be related to the adulterant or a characteristic of interest of the adulterant in the fluid 202, may be conveyed to a detector 212 for analysis and quantification. In some embodiments, the detector 212 is configured to produce an output signal in the form of a voltage that corresponds to the particular characteristic of the fluid 202. In at least one embodiment, the signal produced by the detector 212 and the concentration of the characteristic or adulterant of the fluid 202 may be directly proportional. In other embodiments, the relationship may be a polynomial function, an exponential function, and/or a logarithmic function. The reflected optically interacted light 214, which may be related to characteristics of other components of the fluid 202, can be directed away from detector 212. In alternative configurations, the ICE 208 may be configured such that the reflected optically interacted light 214 can be related to the adulterant, and the transmitted optically interacted light 210 can be related to other components of the fluid 202.

In some embodiments, a second detector 216 can be present and arranged to detect the reflected optically interacted light 214. In other embodiments, the second detector 216 may be arranged to detect the electromagnetic radiation 204, 206 derived from the fluid 202 or electromagnetic radiation directed toward or before the fluid 202. Without limitation, the second detector 216 may be used to detect radiating deviations stemming from an electromagnetic radiation source (not shown), which provides the electromagnetic radiation (i.e., light) to the device 200. For example, radiating deviations can include such things as, but not limited to, intensity fluctuations in the electromagnetic radiation, interferent fluctuations (e.g., dust or other interferents passing in front of the electromagnetic radiation source), coatings on windows included with the optical computing device 200, combinations thereof, or the like. In some embodiments, a beam splitter (not shown) can be employed to split the electromagnetic radiation 204, 206, and the transmitted or reflected electromagnetic radiation can then be directed to one or more ICE 208. That is, in such embodiments, the ICE 208 does not function as a type of beam splitter, as depicted in FIG. 2, and the transmitted or reflected electromagnetic radiation simply passes through the ICE 208, being computationally processed therein, before travelling to the detector 212.

The characteristic(s) of the fluid 202 being analyzed using the optical computing device 200 can be further processed computationally to provide additional characterization information about the fluid 202. In some embodiments, the identification and concentration of each analyte or adulterant in the fluid 202 can be used to predict certain physical characteristics of the fluid 202. For example, the bulk characteristics of a fluid 202 can be estimated by using a combination of the properties conferred to the fluid 202 by each analyte or adulterant.

In some embodiments, the concentration of each adulterant or the magnitude of each characteristic of the adulterant determined using the optical computing device 200 can be fed into an algorithm operating under computer control. The algorithm may be configured to make predictions on how the characteristics of the fluid 202 change if the concentrations of the adulterants or analytes are changed relative to one another. In some embodiments, the algorithm can produce an output that is readable by an operator who can manually take appropriate action, if needed, based upon the output. In some embodiments, the algorithm can take proactive process control by automatically adjusting the flow of a treatment substance being introduced into a flow path or by halting the introduction of the treatment substance in response to an out of range condition.

The algorithm can be part of an artificial neural network configured to use the concentration of each detected adulterant in order to evaluate the overall characteristic(s) of the fluid 202 and predict how to modify the fluid 202 in order to alter its properties in a desired way. Illustrative but non-limiting artificial neural networks are described in commonly owned U.S. patent application Ser. No. 11/986,763 (U.S. Patent App. Pub. No. 2009/0182693), which is incorporated herein by reference. It is to be recognized that an artificial neural network can be trained using samples of adulterants having known concentrations, compositions, and/or properties, and thereby generating a virtual library. As the virtual library available to the artificial neural network becomes larger, the neural network can become more capable of accurately predicting the characteristics of a fluid having any number of adulterants or analytes present therein. Furthermore, with sufficient training, the artificial neural network can more accurately predict the characteristics of the fluid, even in the presence of unknown adulterants.

It is recognized that the various embodiments herein directed to computer control and artificial neural networks, including various blocks, modules, elements, components, methods, and algorithms, can be implemented using computer hardware, software, combinations thereof, and the like. To illustrate this interchangeability of hardware and software, various illustrative blocks, modules, elements, components, methods and algorithms have been described generally in terms of their functionality. Whether such functionality is implemented as hardware or software will depend upon the particular application and any imposed design constraints. For at least this reason, it is to be recognized that one of ordinary skill in the art can implement the described functionality in a variety of ways for a particular application. Further, various components and blocks can be arranged in a different order or partitioned differently, for example, without departing from the scope of the embodiments expressly described.

Computer hardware used to implement the various illustrative blocks, modules, elements, components, methods, and algorithms described herein can include a processor configured to execute one or more sequences of instructions, programming stances, or code stored on a non-transitory, computer-readable medium. The processor can be, for example, a general purpose microprocessor, a microcontroller, a digital signal processor, an application specific integrated circuit, a field programmable gate array, a programmable logic device, a controller, a state machine, a gated logic, discrete hardware components, an artificial neural network, or any like suitable entity that can perform calculations or other manipulations of data. In some embodiments, computer hardware can further include elements such as, for example, a memory (e.g., random access memory (RAM), flash memory, read only memory (ROM), programmable read only memory (PROM), erasable read only memory (EPROM)), registers, hard disks, removable disks, CD-ROMS, DVDs, or any other like suitable storage device or medium.

Executable sequences described herein can be implemented with one or more sequences of code contained in a memory. In some embodiments, such code can be read into the memory from another machine-readable medium. Execution of the sequences of instructions contained in the memory can cause a processor to perform the process steps described herein. One or more processors in a multi-processing arrangement can also be employed to execute instruction sequences in the memory. In addition, hard-wired circuitry can be used in place of or in combination with software instructions to implement various embodiments described herein. Thus, the present embodiments are not limited to any specific combination of hardware and/or software.

As used herein, a machine-readable medium will refer to any medium that directly or indirectly provides instructions to a processor for execution. A machine-readable medium can take on many forms including, for example, non-volatile media, volatile media, and transmission media. Non-volatile media can include, for example, optical and magnetic disks. Volatile media can include, for example, dynamic memory. Transmission media can include, for example, coaxial cables, wire, fiber optics, and wires that form a bus. Common forms of machine-readable media can include, for example, floppy disks, flexible disks, hard disks, magnetic tapes, other like magnetic media, CD-ROMs, DVDs, other like optical media, punch cards, paper tapes and like physical media with patterned holes, RAM, ROM, PROM, EPROM and flash EPROM.

In some embodiments, the data collected using the optical computing devices can be archived along with data associated with operational parameters being logged at a job site. Evaluation of job performance can then be assessed and improved for future operations or such information can be used to design subsequent operations. In addition, the data and information can be communicated (wired or wirelessly) to a remote location by a communication system (e.g., satellite communication or wide area network communication) for further analysis. The communication system can also allow remote monitoring and operation of a process to take place. Automated control with a long-range communication system can further facilitate the performance of remote job operations. In particular, an artificial neural network can be used in some embodiments to facilitate the performance of remote job operations. That is, remote job operations can be conducted automatically in some embodiments. In other embodiments, however, remote job operations can occur under direct operator control, where the operator is not at the job site.

Figure 3:
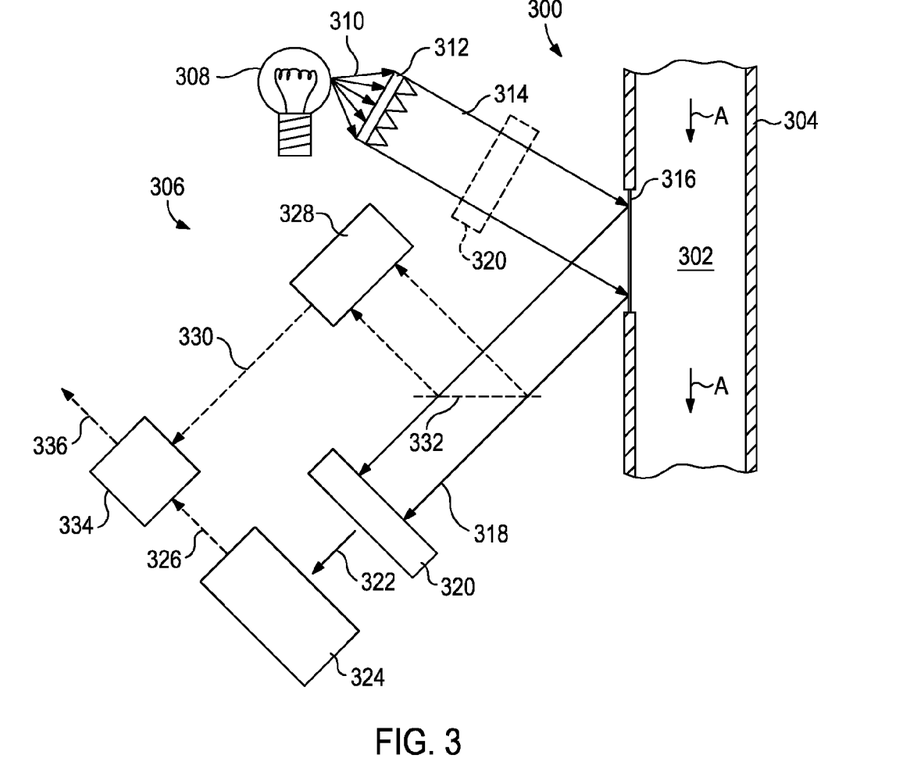
FIG. 3 illustrates an exemplary system for monitoring a fluid, according to one or more embodiments.

Referring now to FIG. 3, illustrated is an exemplary system 300 for monitoring a fluid 302, according to one or more embodiments. In the illustrated embodiment, the fluid 302 may be contained in or otherwise flowing within an exemplary flow path 304. The flow path 304 may be a flow line or a pipeline and the fluid 302 present therein may be flowing in the general direction indicated by the arrows A (i.e., from upstream to downstream). As will be appreciated, however, the flow path 304 may be any other type of flow path, as generally described or otherwise defined herein. For example, the flow path 304 may be a containment or storage vessel and the fluid 302 may not necessarily be flowing in the direction A while the fluid 302 is being monitored.

In at least one embodiment, however, the flow path 304 may form part of an oil/gas pipeline and may be part of a wellhead or a plurality of subsea and/or above-ground interconnecting flow lines or pipes that interconnect various subterranean hydrocarbon reservoirs with one or more receiving/gathering platforms or process facilities. In some embodiments, portions of the flow path 304 may be employed downhole and fluidly connect, for example, a formation and a wellhead. As such, portions of the flow path 304 may be arranged substantially vertical, substantially horizontal, or any directional configuration therebetween, without departing from the scope of the disclosure.

The system 300 may include at least one optical computing device 306, which may be similar in some respects to the optical computing device 200 of FIG. 2, and therefore may be best understood with reference thereto. While not shown, the optical computing device 306 may be housed within a casing or housing configured to substantially protect the internal components of the device 306 from damage or contamination from the external environment. The housing may operate to mechanically couple the device 306 to the flow path 304 with, for example, mechanical fasteners, brazing or welding techniques, adhesives, magnets, combinations thereof or the like. In operation, the housing may be designed to withstand the pressures that may be experienced within or without the flow path 304 and thereby provide a fluid tight seal against external contamination. As described in greater detail below, the optical computing device 306 may be useful in determining a particular characteristic of the fluid 302 within the flow path 304, such as determining a concentration of a known adulterant present within the fluid 302. Knowing the concentration of known adulterants may help determine the overall quality of the fluid 302 and provide an opportunity to remedy potentially undesirable levels of adulterants in the fluid 302.

The device 306 may include an electromagnetic radiation source 308 configured to emit or otherwise generate electromagnetic radiation 310. The electromagnetic radiation source 308 may be any device capable of emitting or generating electromagnetic radiation, as defined herein. For example, the electromagnetic radiation source 308 may be a light bulb, a light emitting device (LED), a laser, a blackbody, a photonic crystal, an X-Ray source, combinations thereof, or the like. In some embodiments, a lens 312 may be configured to collect or otherwise receive the electromagnetic radiation 310 and direct a beam 314 of electromagnetic radiation 310 toward the fluid 302. The lens 312 may be any type of optical device configured to transmit or otherwise convey the electromagnetic radiation 310 as desired. For example, the lens 312 may be a normal lens, a Fresnel lens, a diffractive optical element, a holographic graphical element, a mirror (e.g., a focusing mirror), a type of collimator, or any other electromagnetic radiation transmitting device known to those skilled in art. In other embodiments, the lens 312 may be omitted from the device 306 and the electromagnetic radiation 310 may instead be directed toward the fluid 302 directly from the electromagnetic radiation source 308.

In one or more embodiments, the device 306 may also include a sampling window 316 arranged adjacent to or otherwise in contact with the fluid 302 for detection purposes. The sampling window 316 may be made from a variety of transparent, rigid or semi-rigid materials that are configured to allow transmission of the electromagnetic radiation 310 therethrough. For example, the sampling window 316 may be made of, but is not limited to, glasses, plastics, semi-conductors, crystalline materials, polycrystalline materials, hot or cold-pressed powders, combinations thereof, or the like. In order to remove ghosting or other imaging issues resulting from reflectance on the sampling window 316, the system 300 may employ one or more internal reflectance elements (IRE), such as those described in co-owned U.S. Pat. No. 7,697,141, and/or one or more imaging systems, such as those described in co-owned U.S. patent application Ser. No. 13/456,467, the contents of each hereby being incorporated by reference.

After passing through the sampling window 316, the electromagnetic radiation 310 impinges upon and optically interacts with the fluid 302, including any adulterants present within the fluid 302. As a result, optically interacted radiation 318 is generated by and reflected from the fluid 302. Those skilled in the art, however, will readily recognize that alternative variations of the device 306 may allow the optically interacted radiation 318 to be generated by being transmitted, scattered, diffracted, absorbed, emitted, or re-radiated by and/or from the fluid 302, or one or more adulterants present within the fluid 302, without departing from the scope of the disclosure.

The optically interacted radiation 318 generated by the interaction with the fluid 302 and at least one adulterant present therein may be directed to or otherwise be received by an ICE 320 arranged within the device 306. The ICE 320 may be a spectral component substantially similar to the ICE 100 described above with reference to FIG. 1. Accordingly, in operation the ICE 320 may be configured to receive the optically interacted radiation 318 and produce modified electromagnetic radiation 322 corresponding to a particular characteristic or adulterant of interest of the fluid 302. In particular, the modified electromagnetic radiation 322 is electromagnetic radiation that has optically interacted with the ICE 320, whereby an approximate mimicking of the regression vector corresponding to the characteristic or adulterant in the fluid 302 is obtained.

It should be noted that, while FIG. 3 depicts the ICE 320 as receiving reflected electromagnetic radiation from the fluid 302, the ICE 320 may be arranged at any point along the optical train of the device 306, without departing from the scope of the disclosure. For example, in one or more embodiments, the ICE 320 (as shown in dashed) may be arranged within the optical train prior to the sampling window 316 and equally obtain substantially the same results. In other embodiments, the sampling window 316 may serve a dual purpose as both a transmission window and the ICE 320 (i.e., a spectral component). In yet other embodiments, the ICE 320 may generate the modified electromagnetic radiation 322 through reflection, instead of transmission therethrough.

Moreover, while only one ICE 320 is shown in the device 306, embodiments are contemplated herein which include the use of at least two ICE components in the device 306 configured to cooperatively determine the characteristic or adulterant of interest in the fluid 302. For example, two or more ICE may be arranged in series or parallel within the device 306 and configured to receive the optically interacted radiation 318 and thereby enhance sensitivities and detector limits of the device 306. In other embodiments, two or more ICE may be arranged on a movable assembly, such as a rotating disc or an oscillating linear array, which moves such that the individual ICE components are able to be exposed to or otherwise optically interact with electromagnetic radiation for a distinct brief period of time. The two or more ICE components in any of these embodiments may be configured to be either associated or disassociated with the characteristic or adulterant of interest in the fluid 302. In other embodiments, the two or more ICE may be configured to be positively or negatively correlated with the characteristic or adulterant of interest in the fluid 302. These optional embodiments employing two or more ICE components are further described in co-pending U.S. patent application Ser. Nos. 13/456,264, 13/456,405, 13/456,302, and 13/456,327, the contents of which are hereby incorporated by reference in their entireties.

In some embodiments, it may be desirable to monitor more than one characteristic or adulterant of interest at a time using the device 306. In such embodiments, various configurations for multiple ICE components can be used, where each ICE component is configured to detect a particular and/or distinct characteristic or adulterant of interest. In some embodiments, the characteristic or adulterant can be analyzed sequentially using multiple ICE components that are provided a single beam of electromagnetic radiation being reflected from or transmitted through the fluid 302. In some embodiments, as briefly mentioned above, multiple ICE components can be arranged on a rotating disc, where the individual ICE components are only exposed to the beam of electromagnetic radiation for a short time. Advantages of this approach can include the ability to analyze multiple adulterants within the fluid 302 using a single optical computing device and the opportunity to assay additional adulterants simply by adding additional ICE components to the rotating disc. In various embodiments, the rotating disc can be turned at a frequency of about 10 RPM to about 30,000 RPM such that each adulterant in the fluid 302 is measured rapidly. In some embodiments, these values can be averaged over an appropriate time domain (e.g., about 1 millisecond to about 1 hour) to more accurately determine the characteristics of the fluid 302.

In other embodiments, multiple optical computing devices can be placed at a single location along the flow path 304, where each optical computing device contains a unique ICE that is configured to detect a particular characteristic or adulterant of interest in the fluid 302. In such embodiments, a beam splitter can divert a portion of the electromagnetic radiation being reflected by, emitted from, or transmitted through the fluid 302 and into each optical computing device. Each optical computing device, in turn, can be coupled to a corresponding detector or detector array that is configured to detect and analyze an output of electromagnetic radiation from the respective optical computing device. Parallel configurations of optical computing devices can be particularly beneficial for applications that require low power inputs and/or no moving parts.

Those skilled in the art will appreciate that any of the foregoing configurations can further be used in combination with a series configuration in any of the present embodiments. For example, two optical computing devices having a rotating disc with a plurality of ICE components arranged thereon can be placed in series for performing an analysis at a single location along the length of the flow path 304. Likewise, multiple detection stations, each containing optical computing devices in parallel, can be placed in series for performing a similar analysis.

The modified electromagnetic radiation 322 generated by the ICE 320 may subsequently be conveyed to a detector 324 for quantification of the signal. The detector 324 may be any device capable of detecting electromagnetic radiation, and may be generally characterized as an optical transducer. In some embodiments, the detector 324 may be, but is not limited to, a thermal detector such as a thermopile or photoacoustic detector, a semiconductor detector, a piezo-electric detector, a charge coupled device (CCD) detector, a video or array detector, a split detector, a photon detector (such as a photomultiplier tube), photodiodes, combinations thereof, or the like, or other detectors known to those skilled in the art.

In some embodiments, the detector 324 may be configured to produce an output signal 326 in real-time or near real-time in the form of a voltage (or current) that corresponds to the particular characteristic or adulterant of interest in the fluid 302. The voltage returned by the detector 324 is essentially the dot product of the optical interaction of the optically interacted radiation 318 with the respective ICE 320 as a function of the concentration of the characteristic or adulterant of interest of the fluid 302. As such, the output signal 326 produced by the detector 324 and the concentration of the characteristic or adulterant of interest in the fluid 302 may be related, for example, directly proportional. In other embodiments, however, the relationship may correspond to a polynomial function, an exponential function, a logarithmic function, and/or a combination thereof.

In some embodiments, the device 306 may include a second detector 328, which may be similar to the first detector 324 in that it may be any device capable of detecting electromagnetic radiation. Similar to the second detector 216 of FIG. 2, the second detector 328 of FIG. 3 may be used to detect radiating deviations stemming from the electromagnetic radiation source 308. Undesirable radiating deviations can occur in the intensity of the electromagnetic radiation 310 due to a wide variety of reasons and potentially causing various negative effects on the device 306. These negative effects can be particularly detrimental for measurements taken over a period of time. In some embodiments, radiating deviations can occur as a result of a build-up of film or material on the sampling window 316 which has the effect of reducing the amount and quality of light ultimately reaching the first detector 324. Without proper compensation, such radiating deviations could result in false readings and the output signal 326 would no longer be primarily or accurately related to the characteristic or adulterant of interest.

To compensate for these types of undesirable effects, the second detector 328 may be configured to generate a compensating signal 330 generally indicative of the radiating deviations of the electromagnetic radiation source 308, and thereby normalize the output signal 326 generated by the first detector 324. As illustrated, the second detector 328 may be configured to receive a portion of the optically interacted radiation 318 via a beamsplitter 332 in order to detect the radiating deviations. In other embodiments, however, the second detector 328 may be arranged to receive electromagnetic radiation from any portion of the optical train in the device 306 in order to detect the radiating deviations, without departing from the scope of the disclosure.

In some applications, the output signal 326 and the compensating signal 330 may be conveyed to or otherwise received by a signal processor 334 communicably coupled to both the detectors 320, 328. The signal processor 334 may be a computer including a non-transitory machine-readable medium, and may be configured to computationally combine the compensating signal 330 with the output signal 326 in order to normalize the output signal 326 in view of any radiating deviations detected by the second detector 328. In some embodiments, computationally combining the output and compensating signals 320, 328 may entail computing a ratio of the two signals 320, 328. For example, the concentration of each adulterant or the magnitude of each characteristic determined using the optical computing device 306 can be fed into an algorithm run by the signal processor 334. The algorithm may be configured to make predictions on how the characteristics of the fluid 302 change if the concentrations of the adulterants are changed relative to one another.

In real-time or near real-time, the signal processor 334 may be configured to provide a resulting output signal 336 corresponding to a concentration of the characteristic or adulterant of interest in the fluid 302. The resulting output signal 336 may be readable by an operator who can consider the results and make proper adjustments or take appropriate action, if needed, based upon the measured concentration of adulterants in the fluid 302. In some embodiments, the resulting signal output 328 may be conveyed, either wired or wirelessly, to the user for consideration. In other embodiments, the resulting output signal 336 may be recognized by the signal processor 334 as being within or without a predetermined or preprogrammed range of suitable operation.

For example, the signal processor 334 may be programmed with an impurity profile corresponding to one or more adulterants. The impurity profile may be a measurement of a concentration or percentage of adulterant within the fluid 302. In some embodiments, the impurity profile may be measured in the parts per million range, but in other embodiments, the impurity profile may be measured in the parts per thousand or billion range. If the resulting output signal 336 exceeds or otherwise falls without a predetermined or preprogrammed range of operation for the impurity profile, the signal processor 334 may be configured to alert the user of an excessive amount of adulterant(s) so appropriate corrective action may be taken, or otherwise autonomously undertake the appropriate corrective action such that the resulting output signal 336 returns to a value within the predetermined or preprogrammed range of suitable operation. In some embodiments, the corrective action may include, but is not limited to, adding a treatment substance to the flow path 302, increasing or decreasing the fluid flow within the flow path 302, shutting off the fluid flow within the flow path 302, combinations thereof, or the like.

Those skilled in the art will readily appreciate the various and numerous applications that the system 300, and alternative configurations thereof, may be suitably used with. For example, in one or more embodiments where the fluid 302 is a liquid, such as a hydrocarbon-based liquid corresponding to the oil and gas industry, the optical computing device 306 may be configured to determine one or more known adulterants such as, but not limited to, BTEX compounds (i.e., benzene, toluene, ethylbenzene, and xylenes), volatile organic compounds (VOCs), naphthalene, styrene, water, sand, sulfur compounds, combinations thereof, and the like. In other embodiments, where the fluid 302 is a gas, such as a hydrocarbon-based gas corresponding to the oil and gas industry, the optical computing device 306 may be configured to determine one or more known adulterants such as, but not limited to, hexane, liquefiable hydrocarbons, water, sulfur compounds, black powder-related substances, combinations thereof, and the like. In yet other embodiments, the system 300 may be used to monitor breathable atmosphere and provide early indication of an unhealthy concentration of one or more adulterants (i.e., hazardous substances or chemicals) present within the atmosphere. For example, the system 300 may be configured to provide percentage level measurements of $O_2$, $N_2$, $CO_2$, CO, Ar, methane, or the like.

Figure 4:
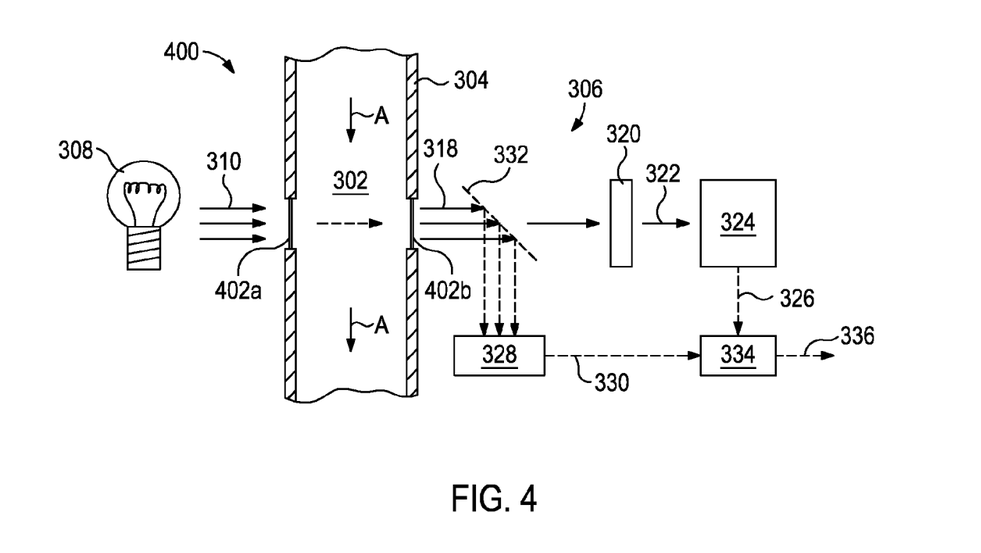
FIG. 4 illustrates another exemplary system for monitoring a fluid, according to one or more embodiments.

Referring now to FIG. 4, illustrated is another exemplary system 400 for monitoring a fluid 302, according to one or more embodiments. The system 400 may be similar in some respects to the system 300 of FIG. 3, and therefore may be best understood with reference thereto where like numerals indicate like elements that will not be described again. As illustrated, the optical computing device 306 may again be configured to determine the concentration of a characteristic or adulterant of interest in the fluid 302 as contained within the flow path 304. Unlike the system 300 of FIG. 3, however, the optical computing device 306 in FIG. 4 may be configured to transmit the electromagnetic radiation through the fluid 302 via a first sampling window 402a and a second sampling window 402b arranged radially-opposite the first sampling window 402a. The first and second sampling windows 402a,b may be similar to the sampling window 316 described above in FIG. 3.

As the electromagnetic radiation 310 passes through the fluid 302 via the first and second sampling windows 402a,b, it optically interacts with the fluid 302 and at least one adulterant present therein. Optically interacted radiation 318 is subsequently directed to or otherwise received by the ICE 320 as arranged within the device 306. It is again noted that, while FIG. 4 depicts the ICE 320 as receiving the optically interacted radiation 318 as transmitted through the sampling windows 402a,b, the ICE 320 may equally be arranged at any point along the optical train of the device 306, without departing from the scope of the disclosure. For example, in one or more embodiments, the ICE 320 may be arranged within the optical train prior to the first sampling window 402a and equally obtain substantially the same results. In other embodiments, one or each of the first or second sampling windows 402a,b may serve a dual purpose as both a transmission window and the ICE 320 (i.e., a spectral component). In yet other embodiments, the ICE 320 may generate the modified electromagnetic radiation 322 through reflection, instead of transmission therethrough. Moreover, as with the system 300 of FIG. 3, embodiments are contemplated herein which include the use of at least two ICE components in the device 306 configured to cooperatively determine the characteristic or adulterant of interest in the fluid 302.

The modified electromagnetic radiation 322 generated by the ICE 320 is subsequently conveyed to the detector 324 for quantification of the signal and generation of the output signal 326 which corresponds to the particular characteristic or adulterant of interest in the fluid 302. As with the system 300 of FIG. 3, the system 400 may also include the second detector 328 for detecting radiating deviations stemming from the electromagnetic radiation source 308. As illustrated, the second detector 328 may be configured to receive a portion of the optically interacted radiation 318 via the beamsplitter 332 in order to detect the radiating deviations. In other embodiments, however, the second detector 328 may be arranged to receive electromagnetic radiation from any portion of the optical train in the device 306 in order to detect the radiating deviations, without departing from the scope of the disclosure. The output signal 326 and the compensating signal 330 may then be conveyed to or otherwise received by the signal processor 334 which may computationally combine the two signals 330, 326 and provide in real-time or near real-time the resulting output signal 336 corresponding to the concentration of the characteristic or adulterant of interest in the fluid 302.

Still referring to FIG. 4, with additional reference to FIG. 3, those skilled in the art will readily recognize that, in one or more embodiments, electromagnetic radiation may be derived from the fluid 302 itself, and otherwise derived independent of the electromagnetic radiation source 308. For example, various substances naturally radiate electromagnetic radiation that is able to optically interact with the ICE 320. In some embodiments, for example, the fluid 302 or the adulterant within the fluid 302 may be a blackbody radiating substance configured to radiate heat that may optically interact with the ICE 320. In other embodiments, the fluid 302 or the adulterant within the fluid 302 may be radioactive or chemo-luminescent and, therefore, radiate electromagnetic radiation that is able to optically interact with the ICE 320. In yet other embodiments, the electromagnetic radiation may be induced from the fluid 302 or the adulterant within the fluid 302 by being acted upon mechanically, magnetically, electrically, combinations thereof, or the like. For instance, in at least one embodiment, a voltage may be placed across the fluid 302 or the adulterant within the fluid 302 in order to induce the electromagnetic radiation. As a result, embodiments are contemplated herein where the electromagnetic radiation source 308 is omitted from the optical computing device 306.

It should also be noted that the various drawings provided herein are not necessarily drawn to scale nor are they, strictly speaking, depicted as optically correct as understood by those skilled in optics. Instead, the drawings are merely illustrative in nature and used generally herein in order to supplement understanding of the systems and methods provided herein. Indeed, while the drawings may not be optically accurate, the conceptual interpretations depicted therein accurately reflect the exemplary nature of the various embodiments disclosed.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

The invention claimed is:

1. A system, comprising:
 a flow path containing a fluid having at least one adulterant present therein;
 at least one integrated computational element configured to optically interact with the fluid and thereby generate optically interacted light; and
 at least one detector arranged to receive the optically interacted light and generate an output signal corresponding to a characteristic of the at least one adulterant within the fluid, wherein:
  the integrated computational element comprises a plurality of alternating layers of two materials having different indices of refraction,
  one of the two materials is selected from the group consisting of silicon, silica, niobium, niobia, germanium, germania, magnesium fluoride, and silicon oxide, and
  a portion of the optically interacted light is transmitted through the integrated computational element.

2. The system of claim 1, further comprising a signal processor communicably coupled to the at least one detector for receiving the output signal, the signal processor being configured to determine the characteristic of the at least one adulterant.

3. The system of claim 1, further comprising an electromagnetic radiation source configured to emit electromagnetic radiation that optically interacts with the fluid.

4. The system of claim 3, wherein the at least one detector is a first detector and the system further comprises a second detector arranged to detect electromagnetic radiation from the electromagnetic radiation source and thereby generate a compensating signal indicative of electromagnetic radiating deviations.

5. The system of claim 4, further comprising a signal processor communicably coupled to the first and second detectors, the signal processor being configured to receive and computationally combine the output and compensating signals in order to normalize the output signal.

6. The system of claim 3, wherein the electromagnetic radiation optically interacts with the at least one integrated computational element after optically interacting with the fluid.

7. The system of claim 3, wherein the electromagnetic radiation optically interacts with the at least one integrated computational element before optically interacting with the fluid.

8. The system of claim 1, wherein the fluid is a liquid.

9. The system of claim 8, wherein the at least one adulterant comprises at least one of benzene, toluene, ethylbenzene, xylene, volatile organic compounds, naphthalene, styrene, water, sand, and sulfur compounds.

10. The system of claim 1, wherein the fluid is a gas.

11. The system of claim 10, wherein the at least one adulterant comprises at least one of hexane, liquefiable hydrocarbons, water, sulfur compounds.

12. The system of claim 1, wherein the characteristic of the at least one adulterant is the concentration of the at least one adulterant in the fluid.

13. A method of monitoring a fluid, comprising:
 containing the fluid within a flow path, the fluid including at least one adulterant present therein;
 optically interacting at least one integrated computational element with the fluid, thereby generating optically interacted light;
 receiving the optically interacted light with at least one detector; and
 generating with the at least one detector an output signal corresponding to a characteristic of the at least one adulterant in the fluid, wherein:
  the integrated computational element comprises a plurality of alternating layers of two materials having different indices of refraction,
  one of the two materials is selected from the group consisting of silicon, silica, niobium, niobia, germanium, germania, magnesium fluoride and silicon oxide, and
  generating the optically interacted light includes transmitting a portion of the optically interacted light through the integrated computational element.

14. The method of claim 13, further comprising emitting electromagnetic radiation from an electromagnetic radiation source, the electromagnetic radiation from the electromagnetic radiation source being configured to optically interact with the fluid and the at least one adulterant.

15. The method of claim 14, further comprising reflecting the electromagnetic radiation emitted from the electromagnetic radiation source off of the fluid.

16. The method of claim 14, further comprising transmitting the electromagnetic radiation emitted from the electromagnetic radiation source through the fluid.

17. The method of claim 14, wherein the at least one detector is a first detector, the method further comprising:
 receiving and detecting with a second detector at least a portion of the electromagnetic radiation emitted from the electromagnetic radiation source;
 generating with the second detector a compensating signal indicative of radiating deviations of the electromagnetic radiation source;
 computationally combining the output signal and the compensating signal with a signal processor communicably coupled to the first and second detectors; and
 normalizing the output signal.

18. The method of claim 13, further comprising:
 receiving the output signal with a signal processor communicably coupled to the at least one detector; and
 determining the characteristic of the at least one adulterant with the signal processor.

19. A method of monitoring a quality of a fluid, comprising:
 optically interacting at least one integrated computational element with a fluid contained within a flow path, thereby generating optically interacted light;

receiving the optically interacted light with at least one detector;

measuring a characteristic of the fluid or at least one known adulterant in the fluid with the at least one detector;

generating an output signal corresponding to the characteristic of the at least one known adulterant; and undertaking at least one corrective action when the characteristic of the at least one adulterant surpasses a predetermined range of suitable operation, wherein:

the integrated computational element comprises a plurality of alternating layers of two materials having different indices of refraction, one of the two materials is selected from the group consisting of silicon, silica, niobium, niobia, germanium, germania, magnesium fluoride, and silicon oxide, and generating the optically interacted light includes transmitting a portion of the optically interacted light through the integrated computational element.

20. The method of claim 19, wherein containing the fluid within the flow path further comprises flowing the fluid within the flow path.

21. The method of claim 19, wherein undertaking the at least one corrective action comprises adding a treatment substance to the flow path.

22. The method of claim 19, wherein undertaking the at least one corrective action comprises increasing or decreasing a flow rate of the fluid within the flow path.

23. The method of claim 19, wherein undertaking the at least one corrective action comprises shutting off a flow of the fluid within the flow path.

24. The method of claim 19, wherein the characteristic of at least one known adulterant is the concentration of the at least one known adulterant in the fluid.

* * * * *